United States Patent
Akatsu

(10) Patent No.: US 12,268,419 B2
(45) Date of Patent: Apr. 8, 2025

(54) ROD FOR SPINAL FIXATION IMPLANT

(71) Applicant: SYNTEC CORPORATION, Iwaki (JP)

(72) Inventor: Kazumi Akatsu, Fukushima (JP)

(73) Assignee: SYNTEC CORPORATION, Iwaki (JP)

( * ) Notice: Subject to any disclaimer, the term of this patent is extended or adjusted under 35 U.S.C. 154(b) by 0 days.

(21) Appl. No.: 18/681,311

(22) PCT Filed: Feb. 16, 2023

(86) PCT No.: PCT/JP2023/005429
§ 371 (c)(1),
(2) Date: Feb. 5, 2024

(87) PCT Pub. No.: WO2023/162847
PCT Pub. Date: Aug. 31, 2023

(65) Prior Publication Data
US 2024/0341813 A1 Oct. 17, 2024

(30) Foreign Application Priority Data
Feb. 28, 2022 (JP) .................................. 2022-030216

(51) Int. Cl.
*A61B 17/70* (2006.01)
(52) U.S. Cl.
CPC ................................ *A61B 17/7005* (2013.01)
(58) Field of Classification Search
None
See application file for complete search history.

(56) References Cited

U.S. PATENT DOCUMENTS 8,641,734 B2 * 2/2014 Moumene .......... A61B 17/7028
606/264
10,420,588 B2 * 9/2019 Murray ................ A61B 17/842
(Continued)

FOREIGN PATENT DOCUMENTS

CN 1882286 A 12/2006
JP 2005-007177 A 1/2005
(Continued)

OTHER PUBLICATIONS

International Search Report corresponding to International Application No. PCT/JP2023/005429, dated Apr. 18, 2023, 2 pages.

*Primary Examiner* — Tessa M Matthews
(74) *Attorney, Agent, or Firm* — Rankin, Hill & Clark LLP

(57) ABSTRACT

A rod for spinal fixation implant having flexibility to reliably support movement of the spine while following movement of the spine with simple configuration. A rod for spinal fixation implant with a screw portion fixed to a vertebral bone and a coupling portion configured to couple the screw portion to the rod, and fixes plural vertebral bones to each other via the rod, the rod for spinal fixation implant includes a layered winding portion 10 configured by layering four layers, in radial direction, of spiral bodies obtained by winding four wires in a spiral shape with space portion inside and gap portion being opened between respective wires in an axial direction; and a rod-shaped core material 3 disposed in the space portion, in which the layered winding portions 10 of four layers are disposed such that spiral directions of the spiral bodies of adjacent layers are opposite to each other.

4 Claims, 3 Drawing Sheets

(56) References Cited

U.S. PATENT DOCUMENTS

| | | | |
|---|---|---|---|
| 2004/0267260 A1* | 12/2004 | Mack | A61B 17/7028 |
| | | | 606/907 |
| 2005/0065516 A1 | 3/2005 | Jahng | |
| 2009/0018583 A1 | 1/2009 | Song et al. | |
| 2009/0281573 A1* | 11/2009 | Biedermann | A61B 17/7029 |
| | | | 606/264 |
| 2014/0200615 A1 | 7/2014 | Yeh | |
| 2018/0221057 A1* | 8/2018 | Akatsu | A61B 17/84 |

FOREIGN PATENT DOCUMENTS

| | | |
|---|---|---|
| JP | 2007-516733 A | 6/2007 |
| KR | 10-2021-0037871 A | 4/2021 |
| WO | 2005/092222 A1 | 10/2005 |

* cited by examiner

FIG.2A
FIG.2B
FIG.2C
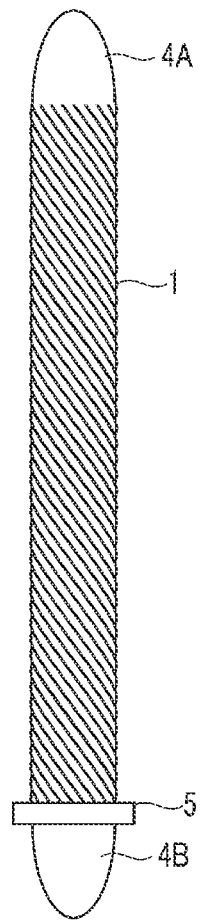

ROD FOR SPINAL FIXATION IMPLANT

TECHNICAL FIELD

The present invention relates to a rod for spinal fixation implant that includes a screw portion fixed to a vertebral bone and a coupling portion that couples the screw portion to the rod, and fixes a plurality of vertebral bones to each other via the rod.

BACKGROUND ART

Conventionally, a rod described in Patent Literature 1 is known as a rod for spinal fixation implant. In the rod for spinal fixation implant described in Patent Literature 1, a spiral of the living body implant is formed as a spiral of a flat metal wire (ribbon wire).

Inside the spiral, a spiral core portion is disposed within at least one partial region of an axial dimension thereof. The spiral core portion is made of a rod and is made of a plurality of separated portions, that is, several rod pieces 9. These have differences in material properties, particularly bending rigidity.

In addition, the spiral is doubled, and an inner one of the two spirals is disposed inside a helix of the other spiral. Here, meandering of the two spirals has rotation directions opposite to each other.

CITATION LIST

Patent Literature

Patent Literature 1: Japanese Patent Application Laid-Open No. 2005-7177

SUMMARY OF INVENTION

Technical Problem

However, with the rod for spinal fixation implant described in Patent Literature 1, there is a problem that the spiral alone is too flexible to ensure fixing property, and on the other hand, when combined with the spiral core portion, the core portion is too hard.

For this reason, the spiral core portion is divided into a plurality of separated portions to be made into a plurality of rod pieces, and the material properties of these rod pieces, particularly, the bending rigidity are different from each other, and thereby the configuration is complicated.

In view of the above circumstances, an object of the present invention is to provide a rod for spinal fixation implant having flexibility to reliably support the movement of the spine while reliably following the movement of the spine with a simple configuration.

Solution to Problem

A rod for spinal fixation implant of a first aspect is a rod for spinal fixation implant that is provided with a screw portion fixed to a vertebral bone and a coupling portion configured to couple the screw portion to the rod, and fixes a plurality of vertebral bones to each other via the rod, the rod for spinal fixation implant includes a layered winding portion configured by layering four layers, in a radial direction, of spiral bodies obtained by winding four wires in a spiral shape with a space portion inside and a gap portion being opened between respective wires in an axial direction; and a rod-shaped core material disposed in the space portion, in which the layered winding portions of four layers are disposed such that spiral directions of the spiral bodies of adjacent layers are opposite to each other.

According to the rod for spinal fixation implant of the first aspect, the wires of four layers of the layered winding portions are disposed such that the spiral directions of the spiral bodies of the adjacent layers are opposite to each other, and thereby it is possible to realize a pressing repulsive force and flexibility required at the time of fixing only by the layered winding portion.

Then, by providing the rod-shaped core material auxiliary in the space portion, it is possible to increase a supporting force without impairing a high fixing property and flexibility.

As described above, according to the rod for spinal fixation implant of the first aspect, it is possible to provide the rod for spinal fixation implant having flexibility to reliably support the movement of the spine while reliably following the movement of the spine with a simple configuration.

In the rod for spinal fixation implant according to the second aspect in the first invention.

both end portions of the rod have R-processed portions in which the layered winding portion and the core material are integrated in a hemispherical shape through melting.

According to the rod for spinal fixation implant of the second aspect, by providing the R-processed portions which are integrated in a hemispherical shape with the layered winding portion and the core material being melted at both end portions of the rod, it is possible to prevent the wire from fraying from the end portion and, at the same time, it is possible to improve insertability with the hemispherical shape and improve handleability.

As described above, according to the rod for spinal fixation implant of the second aspect, it is possible to provide the rod for spinal fixation implant having flexibility to reliably support the movement of the spine while reliably following the movement of the spine with a simple configuration while improving handleability.

In the rod for spinal fixation implant according to the third aspect in the first aspect, cap portions of a hemispherical shape attached to both end portions of the rod are provided.

According to the rod for spinal fixation implant of the third aspect, by providing the cap portion of the hemispherical shape (instead of providing the R-processed portions at both end portions), it is possible to prevent the wire from fraying from the end portion and, at the same time, it is possible to improve insertability with the hemispherical shape and improve handleability.

As described above, according to the rod for spinal fixation implant of the third aspect, it is possible to provide the rod for spinal fixation implant having flexibility to reliably support the movement of the spine while reliably following the movement of the spine with a simple configuration while improving handleability.

In the rod for spinal fixation implant of the fourth aspect in the third aspect, one of the cap portions has a positioning stopper portion having an increased diameter, which is attached to an end portion of the rod in a direction opposite to an insertion direction and stops when abutting against the coupling portion.

According to the rod for spinal fixation implant of the fourth aspect, the positioning stopper portion having an increased diameter that stops when abutting against the coupling portion is formed in one cap portion attached to the end portion of the rod in a direction opposite to the insertion direction. With such a stopper portion, positioning can be easily and reliably realized.

As described above, according to the rod for spinal fixation implant of the fourth aspect, it is possible to provide the rod for spinal fixation implant which improves operability and has flexibility to reliably support the movement of the spine while reliably following the movement of the spine with a simple configuration.

BRIEF DESCRIPTION OF DRAWINGS

FIG. 2A, FIG. 2B, and FIG. 2C are explanatory views illustrating a processing example of an end portion of FIG. 1.

DESCRIPTION OF EMBODIMENTS

A rod for spinal fixation implant of the present embodiment is a rod for spinal fixation implant that is provided with a screw portion fixed to a vertebral bone and a coupling portion configured to couple the screw portion to the rod, and fixes a plurality of vertebral bones to each other via the rod.

For example, the screw portion of the spinal fixation implant has a thread portion screwed from a front side which is a side of the vertebral bone with respect to the vertebral bone, and a spherical head portion which is connected to a rear side which is the opposite side of the vertebral bone with respect to the thread portion.

In addition, the coupling portion of the spinal fixation implant is configured of a hollow cylindrical member, and has U-shaped portions cut into a U-shape that open rearward at two facing portions of a side wall thereof, the rod is disposed at a bottom portion of the U-shaped portion so as to cross the hollow cylinder, and a crown portion in which the head portion is disposed inside the front side of the bottom portion, a hollow cylindrical washer portion inserted inside the crown portion and interposed between the head portion and the rod, and a plug portion that integrates the head portion, the crown portion, the washer portion, and the rod by being screwed onto the rear end portion of the crown portion and pushing the rod are provided.

Figure 1A:
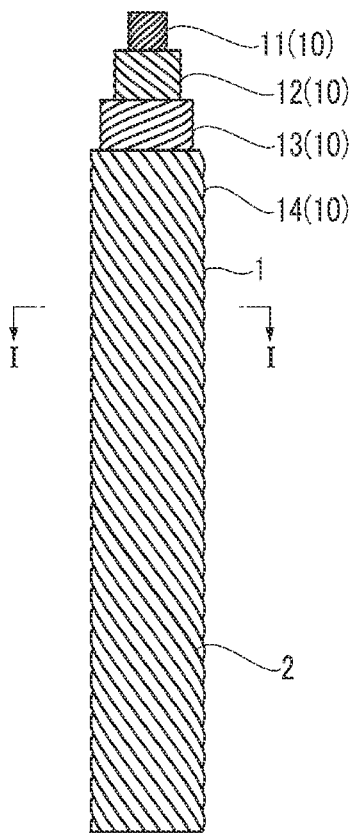
FIG. 1A and FIG. 1B are external views illustrating a rod for spinal fixation implant according to the present embodiment.
Figure 1B:
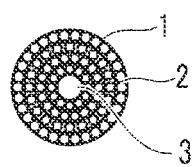

The rod for spinal fixation implant according to the present embodiment is illustrated in FIG. 1A as a front view and FIG. 1B as an end view that is taken along line I-I of FIG. 1A, and a linear member of the present embodiment is a linear member configured by layering four layers, in a radial direction, of layered winding portions 10 obtained by winding a plurality of wires 1 in a spiral shape with a space portion inside and a gap portion 2 being opened between respective wires 1 in an axial direction. The layered winding portion 10 has a plurality of layers as a first spiral body 11 and a second spiral body 12, a third spiral body 13, and a fourth spiral body 14 from the inside.

Here, the number of layers, a pitch of each wire 1 in each layer, and a spiral winding angle θ of each wire 1 in each layer are determined such that in a tensile test regarding the displacement of the linear member against a test force, a displacement d at a half test force f, which is half of the maximum test force F at which the linear member breaks, is a predetermined % of a displacement D at the maximum test force (for example, 3% to 50%, preferably 10% to 30%).

The pitch of the wire 1 is a feed amount per one rotation, and the spiral winding angle θ of the wire 1 is an angle formed by a longitudinal direction of the linear member and a winding direction of the wire as illustrated in FIG. 1.

An alloy in which the wires in each layer contain titanium is, for example, 64 titanium (Ti-6Al-4V), and is configured as follows.

The first spiral body 11 is configured with three wires I having a diameter of 0.5 mm, the pitch is 1.5 mm, and the spiral winding angle θ is approximately 34 degrees in right-handed winding.

The second spiral body 12 is configured with four wires I having a diameter of 0.5 mm, the pitch is 2.0 mm, and the spiral winding angle θ is approximately 32 degrees in right-handed winding.

The third spiral body 13 is configured with five wires I having a diameter of 0.5 mm, the pitch is 2.5 mm, and the spiral winding angle θ is approximately 31 degrees in right-handed winding.

The fourth spiral body 14 is configured with six wires I having a diameter of 0.5 mm, the pitch is 3.0 mm, and the spiral winding angle θ is approximately 30 degrees in right-handed winding.

A rod-shaped core material 3 is disposed in the space portion where the four wires are formed on the inside.

The core material 3 is made of a titanium material (pure titanium material) or a titanium alloy material (6-4 titanium=T-6Al-4V), and bas a diameter of, for example, 1.2 mm.

Next, as illustrated in FIG. 2, in an end portion of the core material 3, from a state of FIG. 2A before processing, as illustrated in FIG. 2B, both end portions of the rod have R-processed portions 4 which are integrated in a hemispherical shape with the layered winding portion 10 and the core material 3 being melted.

Further, as illustrated in FIG. 2C, a stopper portion 5 having an increased diameter may be provided in one R-processed portion 4B of the R-processed portions 4 (rear end side with respect to the insertion direction).

The stopper portion 5 is integrated with the R-processed portion by, for example, extrapolating a ring-shaped member and spot-welding such as brazing joining positions to each other.

In addition to or in place of performing R processing on both end portions of the rod, a cap portion 6 illustrated in FIG. 3 may be connected to both ends of the rod.

Figure 3A:
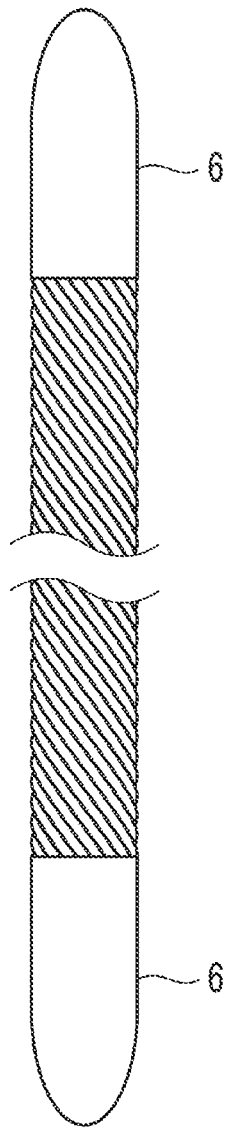
FIG. 3A and FIG. 3B are explanatory views illustrating another processing example of the end portion of FIG. 1.

As illustrated in FIG. 3A, a tip of the cap portion 6 is a hemispherical tubular body, a portion of the tubular body is extrapolated to the end portion of the rod, and the extrapolated portion is crimped from an outer periphery (by caulking) is connected to be integrated.

Figure 3B:
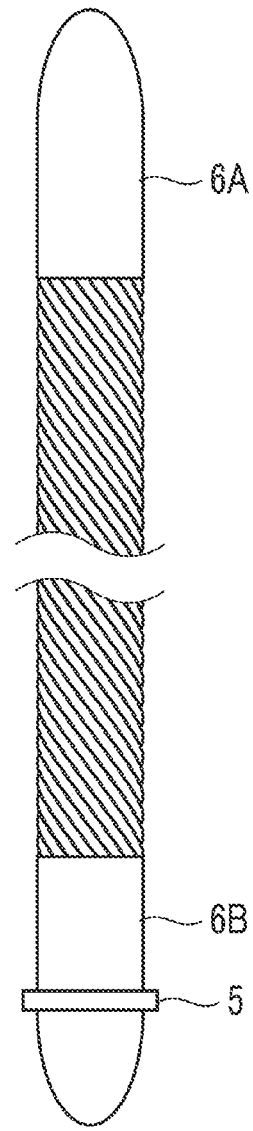

In addition, as illustrated in FIG. 3B, a stopper portion 5 having an increased diameter may be provided in one cap portion 6B of the cap portion 6 (similar to the cap portion 6 of the R processed portion 4B) (rear end side with respect to the insertion direction).

According to the rod for spinal fixation implant configured as described above, the wires of four layers of the layered winding portions 10 are disposed such that the spiral directions of the spiral bodies 11 to 14 of the adjacent layers are opposite to each other, and thereby it is possible to realize the pressing repulsive force and flexibility required at the time of fixing only by the layered winding portion.

Then, by providing the rod-shaped core material 3 auxiliary in the space portion, it is possible to increase the supporting force without impairing a high fixing property and flexibility.

As described above, according to the rod for spinal fixation implant of the present embodiment, it is possible to provide the rod for spinal fixation implant having flexibility to reliably support the movement of the spine while reliably following the movement of the spine with a simple configuration.

Further, by providing the R-processed portions 4 which are integrated in a hemispherical shape with the layered winding portion 10 and the core material 3 being melted at both end portions of the rod, it is possible to prevent the wire from fraying from the end portion and, at the same time, it is possible to improve insertability with the hemispherical shape and improve handleability.

Further, by providing the hemispherical cap portion 6 (instead of providing the R-processed portions 4 at both end portions), it is possible to prevent the wire from fraying from the end portion and, at the same time, it is possible to improve insertability with the hemispherical shape and improve handleability. In addition, during the surgery, the surgeon can match a surgical length of the patient's body, and it is possible to provide the best spinal device.

Further, the positioning stopper portion 5 having an increased diameter that stops when abutting against the coupling portion of the spinal fixation implant is formed in one R processed portion 4B or cap portion 6B attached to the end portion of the rod in a direction opposite to the insertion direction. With such a stopper portion 5, positioning can be easily and reliably realized.

As described above, according to the variation of the rod for spinal fixation implant of the present embodiment, it is possible to provide the rod for spinal fixation implant which improves operability and has flexibility to reliably support the movement of the spine while reliably following the movement of the spine with a simple configuration.

DESCRIPTION OF REFERENCE NUMERALS

1 . . . wire
2 . . . gap portion
4 . . . . R-processed portion
4A . . . R-processed portion on tip side
4B . . . R-processed portion on rear end side
5 . . . stopper portion
6 . . . cap portion
6A . . . cap portion on tip side
6B . . . cap portion on rear end side
10 . . . layered winding portion
11 . . . first spiral body
12 . . . second spiral body
13 . . . third spiral body
14 . . . fourth spiral body.

The invention claimed is:

1. A rod for spinal fixation implant that is provided with a screw portion fixed to a vertebral bone and a coupling portion configured to couple the screw portion to the rod, and fixes a plurality of vertebral bones to each other via the rod, the rod for spinal fixation implant comprising:
   a layered winding portion configured by layering four layers, in a radial direction, of spiral bodies obtained by winding four wires in a spiral shape with a space portion inside and a gap portion being opened between respective wires in an axial direction; and
   a rod-shaped core material disposed in the space portion,
   wherein the layered winding portions of four layers are disposed such that spiral directions of the spiral bodies of adjacent layers are opposite to each other.

2. The rod for spinal fixation implant according to claim 1,
   wherein the rod includes end portions at opposite axial ends of the rod, each of the end portions are processed so that the layered winding portion and the core material at each of the end portions are integrated in a hemispherical shape through melting.

3. The rod for spinal fixation implant according to claim 1, wherein the rod includes end portions at opposite axial ends of the rod, and the rod further comprises:
   a pair of cap portions of a hemispherical shape, each of the pair of cap portions being attached to a respective one of the end portions of the rod.

4. The rod for spinal fixation implant according to claim 3,
   wherein one of the cap portions has a positioning stopper portion having an increased diameter, which is attached to the respective one of the end portions of the rod in a direction opposite to an insertion direction and stops when abutting against the coupling portion.

* * * * *